US010130326B2

(12) United States Patent
Annapragada et al.

(10) Patent No.: US 10,130,326 B2
(45) Date of Patent: Nov. 20, 2018

(54) METHODS AND COMPOSITIONS FOR OBJECTIVELY CHARACTERIZING MEDICAL IMAGES

(71) Applicants: Ananth Annapragada, Manvel, TX (US); Zbigniew Starosolski, Houston, TX (US)

(72) Inventors: Ananth Annapragada, Manvel, TX (US); Zbigniew Starosolski, Houston, TX (US)

( * ) Notice: Subject to any disclaimer, the term of this patent is extended or adjusted under 35 U.S.C. 154(b) by 217 days.

(21) Appl. No.: 13/745,813

(22) Filed: Jan. 20, 2013

(65) Prior Publication Data

US 2013/0190605 A1 Jul. 25, 2013

Related U.S. Application Data

(60) Provisional application No. 61/589,165, filed on Jan. 20, 2012.

(51) Int. Cl.
*A61B 6/00* (2006.01)
*A61B 5/055* (2006.01)
(Continued)

(52) U.S. Cl.
CPC .......... *A61B 6/5247* (2013.01); *A61B 5/0035* (2013.01); *A61B 5/0042* (2013.01);
(Continued)

(58) Field of Classification Search
CPC ..... A61B 5/055; A61B 6/5247; A61B 5/4088; A61B 6/5217; A61B 5/0035;
(Continued)

(56) References Cited

U.S. PATENT DOCUMENTS 4,893,082 A * 1/1990 Letcher, III .................. 324/312
5,204,085 A   4/1993 Vanderipe
(Continued)

FOREIGN PATENT DOCUMENTS

EP   1982733      10/2008
EP   1982733 A1   10/2008
(Continued)

OTHER PUBLICATIONS

VJ Napadow, Q Chen, V Mai, PTC. So, and RJ. Gilbert, "Quantitative Analysis of Three-Dimensional-Resolved Fiber Architecture in Heterogeneous Skeletal Muscle Tissue Using NMR and Optical Imaging Methods," 2001, Biophysical Journal, vol. 80, pp. 2968-2975.*

(Continued)

*Primary Examiner* — Amanda Lauritzen Moher
*Assistant Examiner* — Lisa Kinnard
(74) *Attorney, Agent, or Firm* — Benesch Friedlander Coplan & Aronoff LLP; Benjamen E. Kern; Kraig K. Anderson

(57) ABSTRACT

Methods and compositions are provided for objectively characterizing a pathological lesion in a patient. The method comprises: introducing into the patient a contrast enhancing agent; subjecting the patient to magnetic resonance imaging to obtain an image; and applying a 3-D autocorrelation function to a subdomain of interest of the image to obtain at least one 3-D autocorrelation spectrum. The method may further comprise comparing the at least one 3-D autocorrelation spectrum to a pre-existing 3-D autocorrelation spectrum that is characteristic for the pathological lesion. In one example, the methods and compositions may be useful for identifying and objectively characterizing amyloid plaque deposits characteristic of Alzheimer's Disease.

20 Claims, 7 Drawing Sheets

(51) Int. Cl.
| | |
|---|---|
| *A61B 5/00* | (2006.01) |
| *A61M 5/00* | (2006.01) |
| *A61K 49/04* | (2006.01) |
| *A61K 49/12* | (2006.01) |
| *G01R 33/12* | (2006.01) |
| *A61K 49/00* | (2006.01) |
| *G06T 7/35* | (2017.01) |
| *G06T 7/32* | (2017.01) |
| *G06T 7/00* | (2017.01) |
| *G01R 33/56* | (2006.01) |
| *G01R 33/20* | (2006.01) |
| *A61K 49/10* | (2006.01) |
| *A61K 49/14* | (2006.01) |
| *A61K 49/18* | (2006.01) |
| *A61B 6/03* | (2006.01) |

(52) U.S. Cl.
CPC ............ *A61B 5/055* (2013.01); *A61B 5/4064* (2013.01); *A61B 5/4088* (2013.01); *A61B 6/4417* (2013.01); *A61B 6/481* (2013.01); *A61B 6/5217* (2013.01); *A61K 49/0002* (2013.01); *A61K 49/0084* (2013.01); *A61K 49/0093* (2013.01); *A61K 49/04* (2013.01); *A61K 49/103* (2013.01); *A61K 49/128* (2013.01); *A61K 49/143* (2013.01); *A61K 49/1812* (2013.01); *A61M 5/007* (2013.01); *G01R 33/1269* (2013.01); *G01R 33/1276* (2013.01); *G01R 33/20* (2013.01); *G01R 33/5601* (2013.01); *G06T 7/00* (2013.01); *G06T 7/0008* (2013.01); *G06T 7/0012* (2013.01); *G06T 7/32* (2017.01); *G06T 7/35* (2017.01); *A61B 6/032* (2013.01); *A61B 6/501* (2013.01); *G06T 2207/10088* (2013.01); *G06T 2207/30016* (2013.01)

(58) Field of Classification Search
CPC ... A61B 6/4417; A61B 5/4064; A61B 5/0042; A61K 49/103; A61K 49/143; A61K 49/1812; A61K 49/04; A61K 49/128; A61M 5/007
USPC .......................................................... 600/411
See application file for complete search history.

(56) References Cited

U.S. PATENT DOCUMENTS

| | | | |
|---|---|---|---|
| 5,676,928 A | 10/1997 | Klaveness et al. | |
| 6,067,465 A * | 5/2000 | Foo .................. | G01R 33/56509 324/309 |
| 6,171,614 B1 | 1/2001 | Chaikof et al. | |
| 6,463,315 B1 * | 10/2002 | Klingberg .............. | A61B 5/055 324/309 |
| 6,821,504 B2 | 11/2004 | Wisniewski et al. | |
| 7,138,136 B2 | 11/2006 | Annapragada et al. | |
| 7,208,174 B2 | 4/2007 | Huwyler et al. | |
| 7,713,517 B2 | 5/2010 | Annapragada et al. | |
| 7,785,568 B2 | 8/2010 | Annapragada et al. | |
| 8,357,351 B2 | 1/2013 | Karathanasis et al. | |
| 8,642,013 B2 | 2/2014 | Annapragada et al. | |
| 8,679,531 B2 | 3/2014 | Annapragada et al. | |
| 8,911,708 B2 | 12/2014 | Annapragada et al. | |
| 2003/0147811 A1* | 8/2003 | Wisniewski ......... | A61K 49/085 424/9.34 |
| 2003/0190284 A1 | 10/2003 | Annapragada et al. | |
| 2006/0099141 A1 | 5/2006 | O'Brien et al. | |
| 2006/0120580 A1* | 6/2006 | Makram-Ebeid ..... | G06T 7/0012 382/128 |
| 2007/0031326 A1 | 2/2007 | Shirvan et al. | |
| 2007/0160658 A1 | 7/2007 | Connor et al. | |
| 2007/0292354 A1 | 12/2007 | Port | |
| 2008/0119718 A1* | 5/2008 | Hundley et al. .............. | 600/407 |
| 2008/0131369 A1 | 6/2008 | Annapragada et al. | |
| 2008/0212887 A1* | 9/2008 | Gori ..................... | G06K 9/4619 382/248 |
| 2009/0123047 A1 | 5/2009 | Yfantis | |
| 2009/0155181 A1* | 6/2009 | Rowe .............................. | 424/9.3 |
| 2009/0263326 A1 | 10/2009 | Karathanasis et al. | |
| 2009/0311191 A1 | 12/2009 | Annapragada et al. | |
| 2010/0105608 A1* | 4/2010 | Gazit .................. | C07K 5/06078 514/17.8 |
| 2010/0135544 A1* | 6/2010 | Mattiuzzi .................. | G06T 7/33 382/128 |
| 2010/0190831 A1 | 7/2010 | Shi et al. | |
| 2010/0286067 A1 | 10/2010 | Defrees | |
| 2011/0093960 A1 | 4/2011 | Edwards et al. | |
| 2011/0172538 A1* | 7/2011 | Sumi ........................ | A61B 8/06 600/453 |
| 2011/0306845 A1* | 12/2011 | Osorio .......................... | 600/300 |
| 2011/0311457 A1 | 12/2011 | Skerrett et al. | |
| 2012/0003159 A1 | 1/2012 | Annapragada et al. | |
| 2012/0039810 A1* | 2/2012 | Gorenstein et al. ........... | 424/9.1 |
| 2012/0258044 A1 | 10/2012 | Annapragada et al. | |
| 2013/0289140 A1 | 10/2013 | Mbebi-Liegeois et al. | |
| 2014/0161875 A1 | 6/2014 | Winderickx et al. | |

FOREIGN PATENT DOCUMENTS

| | | | | |
|---|---|---|---|---|
| EP | 2694116 | 2/2014 | | |
| WO | 2002028441 | 4/2002 | | |
| WO | 2002028441 | 6/2002 | | |
| WO | 2005107820 | 11/2005 | | |
| WO | 2009073236 | 6/2009 | | |
| WO | 2009073896 | 6/2009 | | |
| WO | 2010107990 | 9/2009 | | |
| WO | 2009150686 | 12/2009 | | |
| WO | 2010017094 | 2/2010 | | |
| WO | 2010107990 | 9/2010 | | |
| WO | 2011045415 | 4/2011 | | |
| WO | WO 2011045415 A2 * | 4/2011 | ......... | A61K 51/0453 |
| WO | 2011159297 | 12/2011 | | |
| WO | 2012119117 | 9/2012 | | |
| WO | 2012139080 | 10/2012 | | |
| WO | 2013110013 | 8/2013 | | |
| WO | 2014152229 | 9/2014 | | |
| WO | 2016057812 | 4/2016 | | |

OTHER PUBLICATIONS

K Sellers, "Why Derivatize? Improve GC Separations with Derivatization", 2007, http://www.restek.com/pdfs/adv_2007_03_07.*

T van Groen, K Wiesehan, SA. Funke, I Kadish, L Nagel-Steger,and D Willbold, "Reduction of Alzheimer's Disease Amyloid Plaque Load in Transgenic Mice by D3, a d-Enantiomeric Peptide Identified by Mirror Image Phage Display", 2008, ChemMedChem, vol. 3, pp. 1848-1852.*

T Montez, S-S Poil, BF Jones, I Manshanden, JPA Verbunt, BW van Dijk, AB Brussaard, A van Ooyen, CJ Stam, P Scheltens, and K Linkenkaer-Hansen, "Altered temporal correlations in parietal alpha and prefrontal theta oscillations in early-stage Alzheimer disease", 2009, www.pnas.org_cgi_doi_10.1073_pnas.0811699106.*

SL Fossheim, AK Fahlvik, J Klaveness, RN Muller, "Paramagnetic Liposomes as MRI Contrast Agents: Influence of Liposomal Physicochemical Properties on the In Vitro Relaxitivity", 1999, Magnetic Resonance Imaging, vol. 17, No. 1, pp. 83-89.*

PM Thompson, J Moussai, S Zohoori, A Goldkorn, AA Khan, MS Mega, GW Small, JL Cummings, AW Toga, "Cortical Variability and Assymetry in Normal Aging and Alzheimer's Disease", 1998, pp. 492-509; http://cercor.oxfordjournals.org/content/8/6/492.long.*

Hsu et al., Scientific Reports | 7: 5035 | DOI:10.1038/s41598-017-05390-1, published Jul. 11, 2017.*

NIH website; accessed Aug. 20, 2017, https://www.nia.nih.gov/health/alzheimers-disease-fact-sheet#diagnose.*

Hardy et al. "Coronary Angiography by Real-Time MRI with Adaptive Averaging." Magnetic Resonance in Medicine 44: 940-946 (2000).*

(56) References Cited

OTHER PUBLICATIONS

Wald Michael et al., "Spatial autocorrelation and mean intercept length analysis of trabecular bone anisotropy applied to in vivo magnetic resonance imaging," Medical Physics, AIP, Melville, NY US, vol. 34, No. 3, Feb. 27, 2007 pp. 1110-1120.
European Search Report, dated Jul. 29, 2014, related to European Patent Application No. 13738451.7.
Ding, et al. "Folate Receptor-targeted Fluorescent Paramagnetic Bimodal Liposomes for Tumor Imaging" Int. J. Nanomedicine, 2011, 6, 2513-2520.
Written opinion and search report from related PCT Application No. PCT/US2012/032649.
Written opinion and search report from related PCT Application No. PCT/US2013/022336.
Winter, et al., "Improved Molecular Imaging Contrast Agent for Detection of Human Thrombus" Mag. Res. Med. 2003, 50, 411-416.
Thompson, et al., "Cortical Variability and Asymmetry in Normal Aging and Alzheimer's Disease" Cerebral Cortex 1998, 8, 492-509.
McNeely, et al. "Decreased Circulation Time Offsets Increased Efficacy of PEGylated Nanocarriers Targeting Folate Receptors of Glioma" Nanotechnology 2007, 18, 1-11.
Burke, et al., "Imaging of Pulmonary Embolism and t-PA Therapy Effects Using MDCT and Liposomal Iohexol Blood Pool Agent: Preliminary Results in a Rabbit Model" Academic Radiol. 2007, 14, 355-362.
Kao, et al., "Long-Residence-Time Nano-Scale Liposomal Iohexol for X-ray-Based Blood Pool Imaging" Acad. Radiol. 2003, 10, 475-483.
Ding, et al., "Folate Receptor-Targeted Fluorescent Paramagnetic Bimodal Liposomes for Tumor Imaging" Int. J. Nanomed. 2011, 6, 2513-2520.
European Search Report issued in EP2756459, dated Jul. 29, 2014.
Skaat, et al., "Synthesis of Fluorescent-Maghemite Nanoparticles as Multimodal Imaging Agents for Amyloid-Beta Fibrils Detection and Removal by a Magnetic Field" Biochem. Biophys. Res. Commun. 2009, 386, 645-649.
Van Groen, el al., "Reduction of Alzheimer's Disease Amyloid Plaque Load in Transgenic Mice by D3, a D-Enantiomeric Peptide Identified by Mirror IMage Phage Display" Chem. Med. Chem. 2008, 3, 1848-1852.

Written Opinion and International Search Report from PCT Application No. PCT/US12/032649 dated Jun. 20, 2012.
Mukundan, et al., "A Liposomal Nanoscale Contrast Agent for Preclinical CT in Mice" AJR Am. J. Roentgenol. 2006, 186, 300-307.
Karathanasis, et al., "Multifunctional Nanocarriers for Mammographic Quantification of Tumor Dosing and Prognosis of Breast Cancer Therapy" Biomaterials 2008, 29, 4815-4822.
Karathanasis, et al., "Imaging Nanoprobe for Prediction of Outcome of Nanoparticle Chemotherapy by Using Mammography" Radiology 2009, 250, 398-406.
Karathanasis, et al., "Tumor Vascular Permeability to a Nanoprobe Correlates to Tumor-Specific Expression Levels of Angiogenic Markers" PLoS One 2009, 4, 5843.
Samei, et al., "Micro-CT Imaging of Breast Tumors in Rodents Using a Liposomal, Nanoparticle Contrast Agent" Int. J. Nanomedicine 2009, 4, 277-282.
Klunk, et al., Imaging AB Plaques in Living Transgenic Mice with Multiphoton Microscopy and Methoxy-XO4, a Systemically Administered Congo Red Derivative J. Neuropath. Exp. Neurol. 2002, 61, 797-805.
European Search Report in EP2694116, dated Apr. 29, 2015.
Napadow, et al., "Quantitative Analysis of Three-Dimensional-Resolved Fiber Architecture in Heterogeneous Skeletal Muscle Tissue Using NMR and Optical Imaging Methods" Biophys. J. 2001, 80, 2968-2975.
Fosshein, et al., "Paramagnetic Liposomes as MRI Contrast Agents: Influence of Liposomal Physicochemical Properties on the in Vitro Relaxivity" Mag. Res. Imag. 1999, 17, 83-89.
Montez, et al., "Altered temporal correlations in parietal alpha and prefrontal theta oscillations in early-stage Alzheimer Disease" Proceed. Nat. Acad. Sci. 2009, 1-6.
Written Opinion and International Search Report from PCT Application No. PCT/US15/54732 dated Jan. 11, 2016.
Wald, et al., "Spatial Autocorrelation and Mean Intercept Length Analysis of Trabecular Bone Anisotropy Applied to in vivo Magnetic Resonance Imaging" Med. Phys. 2007, 34, 1110-1120.
Written Opinion and International Search Report from PCT Application No. PCT/US13/22336 dated Apr. 1, 2013.
Sellers, "Why Derivatize?", downloaded from http://www.restek.com/pdfs/adv_2007_03_07.

* cited by examiner

METHODS AND COMPOSITIONS FOR OBJECTIVELY CHARACTERIZING MEDICAL IMAGES

CROSS-REFERENCE TO RELATED APPLICATIONS

This application claims priority from U.S. Provisional Patent Application No. 61/589,165, filed on Jan. 20, 2012, which is incorporated by reference herein in its entirety.

BACKGROUND

Medical images are routinely acquired in the screening, diagnosis, and treatment of many diseases. A variety of imaging techniques exist, including, for example, magnetic resonance imaging (MRI), X-ray, computed tomography (CT), ultrasonic imaging, and nuclear medicine. In particular, MRI, X-ray, and CT produce images of anatomical structures, such as pathological lesions.

One limitation of current imaging techniques is that few methods exist to objectively characterize the structure (in the case of pathological lesions) imaged without the need for human interpretation. One attempted method for objective image analysis is the 2-dimensional (2-D) autocorrelation function. However, for a variety of reasons, the 2-D autocorrelation function is practically meaningless in the context of a 3-dimensional (3-D) image.

A system and method are needed for using a morphometric index-a measure of the morphology of certain medical images—that objectively characterizes the images. Thus, a system and method are provided herein for using the 3-D autocorrelation function to objectively characterize medical images.

SUMMARY

In one embodiment, a method for characterizing a pathological lesion in a patient is provided, the method comprising: introducing into the patient a contrast enhancing agent; subjecting the patient to MRI to obtain an image; and applying a 3-D autocorrelation function to a subdomain of interest of the image to obtain at least one 3-D autocorrelation spectrum. The method may further comprise comparing the at least one 3-D autocorrelation spectrum to a pre-existing 3-D autocorrelation spectrum that is characteristic for the pathological lesion.

In another embodiment, a method for detecting amyloid plaque deposition on a patient's brain is provided, the method comprising: introducing into the patient a nanoparticle contrast enhancing agent; subjecting the patient to MRI to obtain an image; and applying a 3-D autocorrelation function to a subdomain of interest of the image to obtain at least one 3-D autocorrelation spectrum. The method may further comprise comparing the at least one 3-D autocorrelation spectrum to a pre-existing 3-D autocorrelation spectrum that is characteristic for amyloid plaque deposition on a brain.

In another embodiment, a method for diagnosing Alzheimer's Disease in a patient is provided, the method comprising: introducing into the patient a nanoparticle contrast enhancing agent, the nanoparticle contrast enhancing agent comprising: liposomes, the liposomes comprising: 1,2-dipalmitoyl-sn-glycero-3-phosphocholine (DPPC), Gd-DTPA bis(stearylamide) (Gd-DTPA-BSA), cholesterol, and 1,2-distearoyl-sn-glycero-3-phosphoethanolamine-N-[methoxy(-poly(ethylene glycol))-2000] (mPEG2000-DSPE); subjecting the patient to MRI to obtain an image; and applying a 3-D autocorrelation function to a subdomain of interest of the image to obtain at least one 3-D autocorrelation spectrum. The method may further comprise comparing the at least one 3-D autocorrelation spectrum to a pre-existing 3-D autocorrelation spectrum that is characteristic for Alzheimer's Disease.

BRIEF DESCRIPTION OF THE DRAWINGS

In the accompanying figures, experimental data are given that, together with the detailed description provided below, describe example embodiments of the claimed invention.

DETAILED DESCRIPTION

Figure 1:
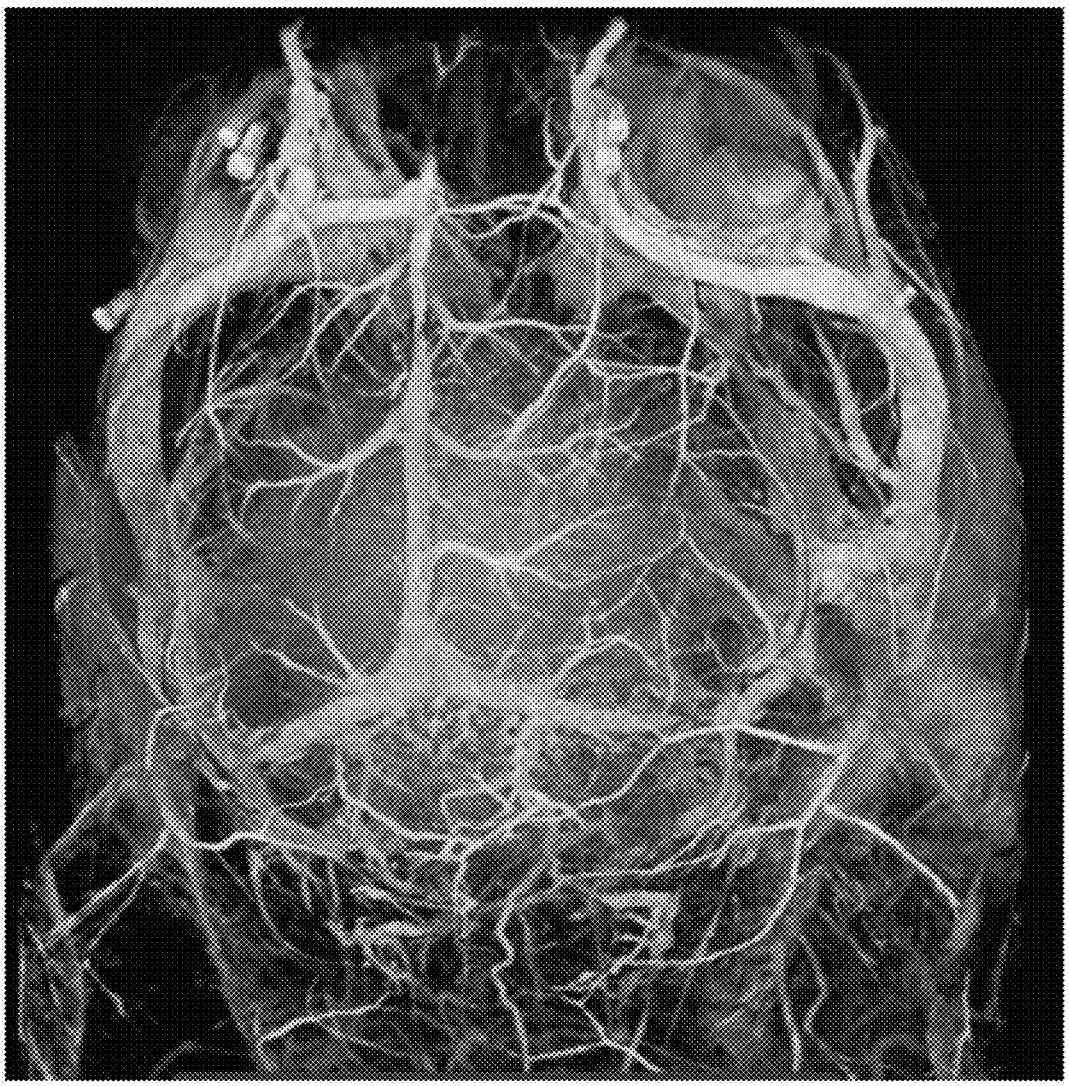
FIG. 1 illustrates a cerebral magnetic resonance angiography in a C57BL/6 mouse.

Methods and compositions for objectively characterizing pathological lesion(s) in a patient are provided. In one embodiment, the method comprises introducing into the patient a contrast enhancing agent; subjecting the patient to MRI to obtain an image; and applying a 3-D autocorrelation function to a subdomain of interest of the image to obtain at least one 3-D autocorrelation spectrum. The method may further comprise comparing the at least one 3-D autocorrelation spectrum to a pre-existing 3-D autocorrelation spectrum that is characteristic for the pathological lesion(s).

Autocorrelation in higher dimensions is defined as:

$$A(\tau_x, \tau_y, \tau_z) = \frac{\sum_x \sum_y \sum_z S(x, y, z) S(x - \tau_x, y - \tau_y, z - \tau_z)}{\sum_x \sum_y \sum_z (S(x, y, z))^2}$$

This quantity is a direct measure of the value of a function S at any location in the domain with respect to its value at some distance $\tau$ away. From its origins as a method of analyzing time, $\tau$, the spatial displacement, is also called the "delay" coordinate. This formally definitive expression, however, is numerically very intensive, with the number of operations per function evaluation scaling as $\eta^2$, where $\eta$ is the number of delay intervals to be used. Thus, 1-D data is relatively straightforward to compute, but 2-D data scales as $\eta^4$, and 3-D data as $\eta^6$, leading to onerous computational demands. For higher order autocorrelation functions, the Wiener-Khinchin theorem becomes necessary, which shows that the autocorrelation is equal to the Fourier transform of the power spectrum of the original function. Using the Fast Fourier Transform algorithm, the computational load scales as $2\eta \log \eta$, a much more practicable situation.

The physical interpretation of the autocorrelation function is straightforward. It essentially measures the behavior of a function at a certain distance from any starting point in the domain. Thus, at a zero delay coordinate, the autocorrelation is always 1, since the function at any point is equal to itself. Purely random functions display $\{A:A_{\tau=0}=1; A_{\tau\neq 0}=0\}$. Inherent decays and periodicities in functions are amplified in the autocorrelation, and automatically scale to a range of $\{0,1\}$.

In one exemplary embodiment of the method, amyloid plaque deposition on a patient's brain may be detected. Thus, a nanoparticle contrast enhancing agent is introduced to the patient; and the patient is subjected to MRI to obtain an image.

If the imaging technique of choice is MRI, the contrast enhancing agent may comprise an MR-effective nanoparticle contrast enhancing agent such as a gadolinium complex having long circulating properties, such as, for example, the dual gadolinium liposomal agent described in Ghaghada, K. B. et al., "New dual mode gadolinium nanoparticle contrast agent for magnetic resonance imaging." *PloS One*, 4(10), e7628. Doi:10.1371/journal.pone.0007628, which is incorporated by reference herein in its entirety. In one embodiment, the dual gadolinium liposomal agent is less than about 200 nm in average diameter. In one embodiment, the dual gadolinium liposomal agent is less than about 175 nm in average diameter. In one embodiment, the dual gadolinium liposomal agent is less than about 150 nm in average diameter. In one embodiment, the dual gadolinium liposomal agent is about 100 nm in average diameter. Another suitable MR-effective agent may include ABLAVAR® (gadofosveset trisodium) (Lantheus Medical Imaging, Inc. N. Billerica, Mass.), a stable gadolinium diethylenetriaminepentaacetic acid (GdDTPA) chelate derivative with a diphenylcyclohexylphosphate group. Another suitable MR-effective agent may include an agent comprising liposomes, the liposomes comprising: a phospholipid (e.g., DPPC); a phospholipid that is derivatized with a polymer (e.g., a PEGylated phospholipid such as mPEG2000-DSPE); and cholesterol, wherein the liposomes encapsulate, chelate, or encapsulate and chelate gadolinium in various forms.

Once an image is obtained, a 3-D autocorrelation function may be applied to a subdomain of interest of the image to obtain at least one 3-D autocorrelation spectrum. In other words, in one embodiment, the 3-D autocorrelation function may be applied in a local sense, to a carefully selected subdomain, and the computation so restricted, rather than calculating the autocorrelation function over the totality of the image.

The method may further comprise comparing the at least one 3-D autocorrelation spectrum to a pre-existing 3-D autocorrelation spectrum that is characteristic for amyloid plaque deposition on a brain.

Amyloid plaque deposits are a major neuropathological hallmark of Alzheimer's Disease, and manifest long before clinical symptoms are discernible. Thus, in one embodiment, the method may be useful for diagnosing Alzheimer's Disease in living patients.

In one embodiment, nanoparticle contrast enhancing agent may be administered to a patient with subsequent MRI and 3-D autocorrelation in order to establish a baseline spectrum of a patient's normal image and spectrum. In one embodiment, the patient is healthy when the baseline spectrum is established. Thus, subsequent administration may be used then, for example, to determine deviations from the baseline spectrum indicative of a disease state. In another embodiment, the patient may already have been diagnosed with a disease known or suspected to alter the patient's spectrum. In that case, subsequent administration may be used, for example, to gauge disease progression or to determine the effectiveness of treatment. In yet another embodiment, the baseline spectrum may reflect a sampling of healthy or diseased patients other than the patient under study. Thus, administration to the patient may be used, for example, to determine deviations from, or similarities to, the baseline spectrum or spectra indicative of a disease state or the absence of a disease state.

EXAMPLES

Certain embodiments are described below in the form of examples. It is impossible to depict every potential application of the invention. Thus, while the embodiments are described in considerable detail, it is not the intention to restrict or in any way limit the scope of the appended claims to such detail, or to any particular embodiment.

Example 1—Preparation of Dual Gd Liposomes

A lipid mixture comprising DPPC, Gd-DTPA-BSA, cholesterol, and mPEG2000-DSPE in the molar ratio 30:25:40:5 was dissolved in a chloroform:methanol (1:1 v/v) mixture. The solvent mixture was evaporated to dryness under vacuum and the lipid contents were hydrated with a solution of gadobenate dimeglumine (MULTIHANCE®, Gd-BOPTA, 500 mM Gd, Bracco Diagnostics Inc., Monroe Township, N.J.) to achieve a lipid concentration of 40 mM. The solution was stirred for 90 min at 60° C. and then sequentially extruded with five passes through a 400 nm NUCLEPORE™ membrane (Sigma-Aldrich, St. Louis, Mo.), seven passes through a 200 nm NUCLEPORE™ membrane, and ten passes through a 100 nm NUCLEPORE™ membrane. The resulting solution was diafiltered using a MICROKROS® module (Spectrum Laboratories, Rancho Dominguez, Calif.) of 500 kDa molecular weight cut-off to remove unencapsulated and unchelated Gd-chelate molecules. Size analysis of the liposomes indicated particles of approximately 100 nm in diameter. The low polydispersity index for various formulations indicated narrow size distributions. More than 95% of the liposomes were below 150 nm in diameter.

Example 2—MRI of Mouse Brain Vasculature

Cerebral angiograms were acquired in C57BL/6 mice using the dual Gd liposomes of Example 1 at a dose of 200 mg lipid/kg, injected intravenously. Imaging was conducted using FSPGR (Fast Spoilt Gradient) studies using a $512^3$ image matrix, and the following parameters: repetition time (TR)=20.0 ms; echo time (TE)=3 ms; flip angle (FA)=30°; field of view (FOV)=30 mm×30 mm×30 mm; and images were generated with anisotropic voxel size of 60μ. FIG. 1 shows an MRI image of the cranial vasculature in a mouse. In FIG. 1, the entire cranial vasculature is clearly visible, including the circle of Willis and microvessels to about the 4th generation of bifurcation past the carotid.

Example 3—Morphological Analysis

Figure 2:
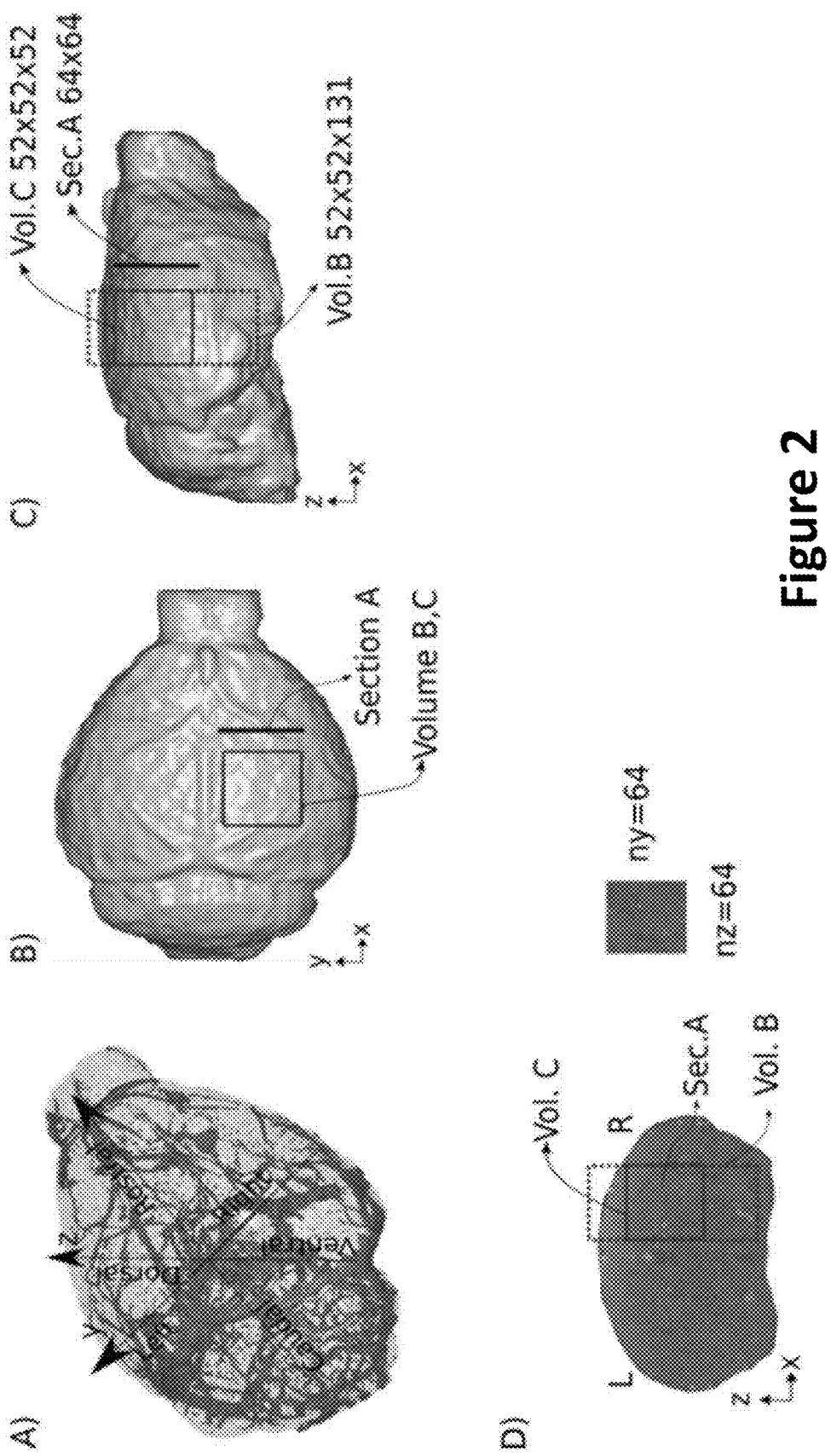
FIG. 2 illustrates a 2-dimensional view of a subdomain of the brain vasculature shown in the cerebral magnetic resonance angiography of FIG. 1.

To test the sensitivity of three morphometric techniques (multi-fractality, lacunarity, and 2-D autocorrelation), algorithms were implemented for each, in MATLAB (MathWorks, Natick, Mass.). A 2-D section of the mouse brain vasculature from FIG. 1 was used, and is shown in FIG. 2. The T1 weighted image with liposomal contrast was windowed to show vascular signal, but no soft tissue contrast. The section was placed dextro-rostral to centerline, and included vasculature in portions of the thalamus and hippocampus. To test the sensitivity of the morphometric measures to the presence of vascular anomalies, the sectional image was digitally manipulated to introduce below-threshold "holes." Such holes would result when amyloid plaque deposits distort blood vessels. Three such cases were created, one in which a single large "hole" about 1 mm×0.5 mm was created in the section; the second in which a single small hole, about 100μ×200μ, was created; and the third in which multiple small holes were created. The holes were created using an algorithm that randomly generates clusters of spheres, the diameters of which are distributed normally about a mean, similar to a diffusion-limited aggregate, in order to simulate amyloid plaques. When the aggregates are superimposed on the voxel structure of the vascular image, they result in total and partial voxel occlusion, and the voxel intensities are either totally or fractionally reduced to baseline.

Figure 3A:
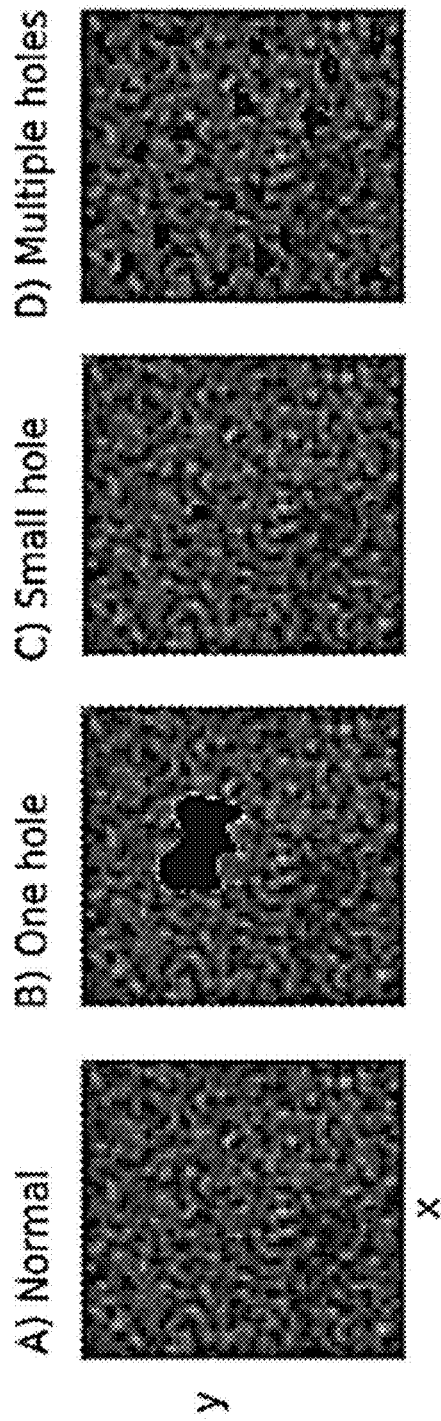
FIG. 3a illustrates results of multi-fractality and lacunarity analysis of the subdomain of FIG. 2, wherein the subdomain has been digitally manipulated to introduce synthetic "holes" that simulate amyloid plaques.
Figure 3A:
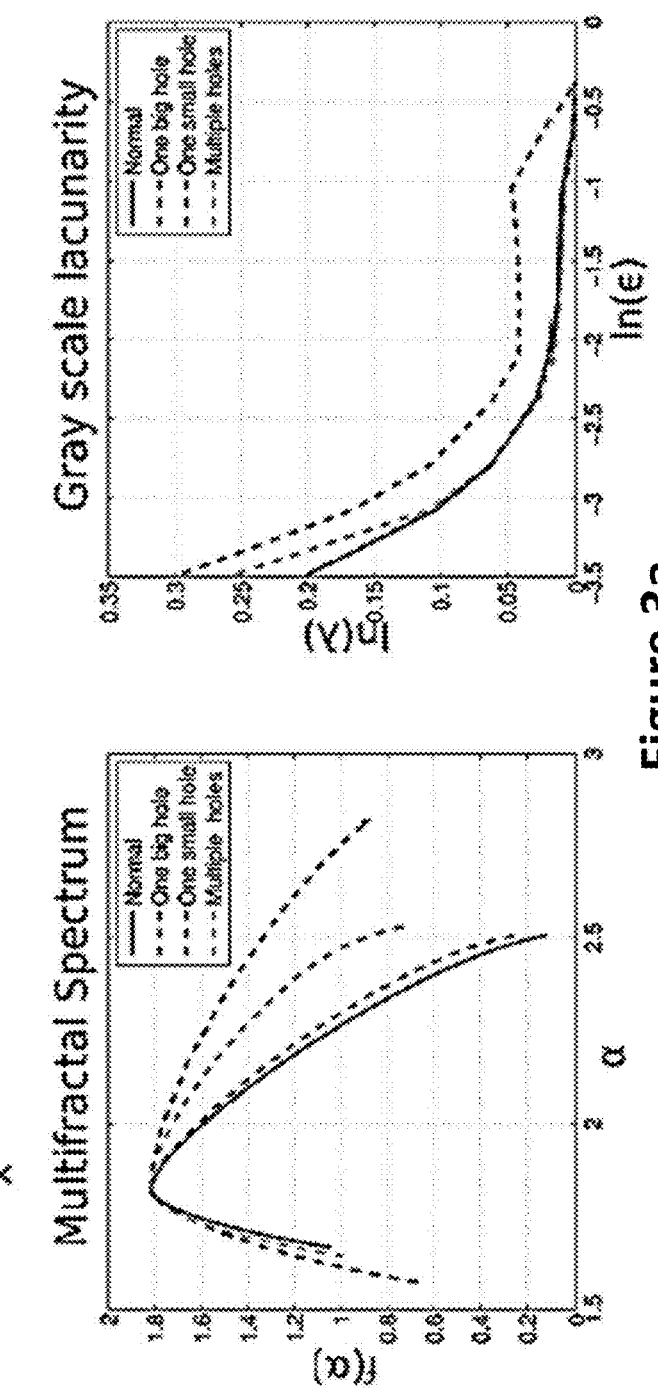
Figure 3B:
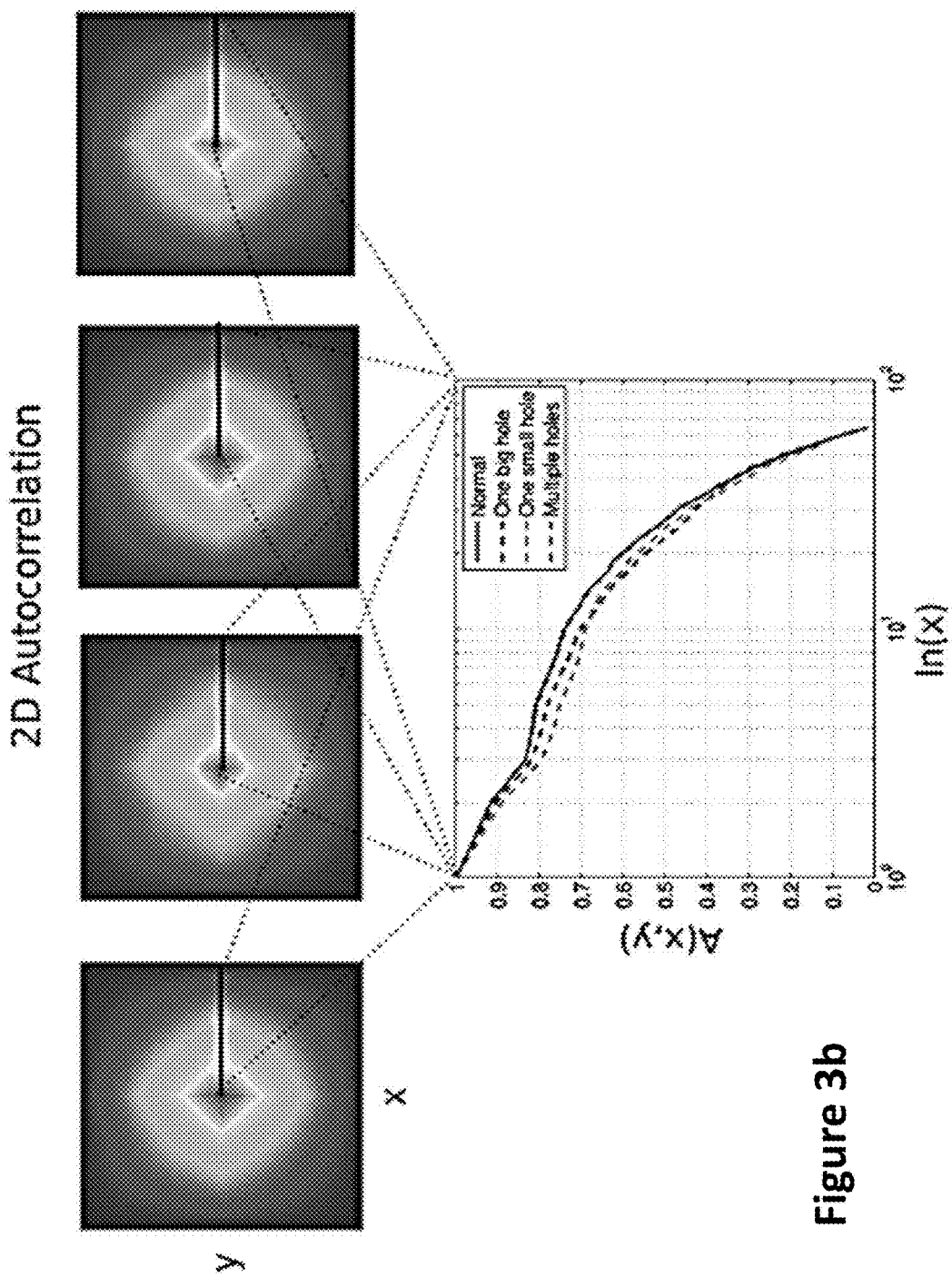
FIG. 3b illustrates results of 2-D autocorrelation analyses of the subdomain of FIG. 2, wherein the subdomain has been digitally manipulated to introduce synthetic "holes" that simulate amyloid plaques.

The results are shown in FIG. 3a and FIG. 3b, Cases A (normal), B (large hole), C (small hole), and D (several small holes). In each case, three morphometric analyses were performed: multi-fractal spectrum, lacunarity, and 2-D autocorrelation. The images clearly show multi-fractal behavior as evidenced by the characteristic inverted U shape of the spectrum. While introducing one large hole occupying about 2% of the area causes a dramatic change in the multi-fractal spectrum, such a large change is unrealistic to expect in actual amyloid deposition. At smaller area fractions, the multi-fractal spectrum is not sensitive. The lacunarity is less sensitive still, and only shows a difference for the largest hole set. The 2-D autocorrelation spectra show very little change as well.

Example 4—Volume-Based Morphometry

Cerebral vascular images from seven different mice were chosen. Three of the mice were APP/PSEN1 mice ranging from 14 to 21 months of age, and exhibiting significant cognitive deficit and signs of dementia. Two of the mice were non-transgenic siblings in the same general age range. Two of the mice were normal C57BL/6 mice that were approximately ten months old. MR cerebral angiograms of each of these mice were acquired using the blood pool contrast agent of Example 1. Acquisition sequences were as described in Example 2.

Figure 4:
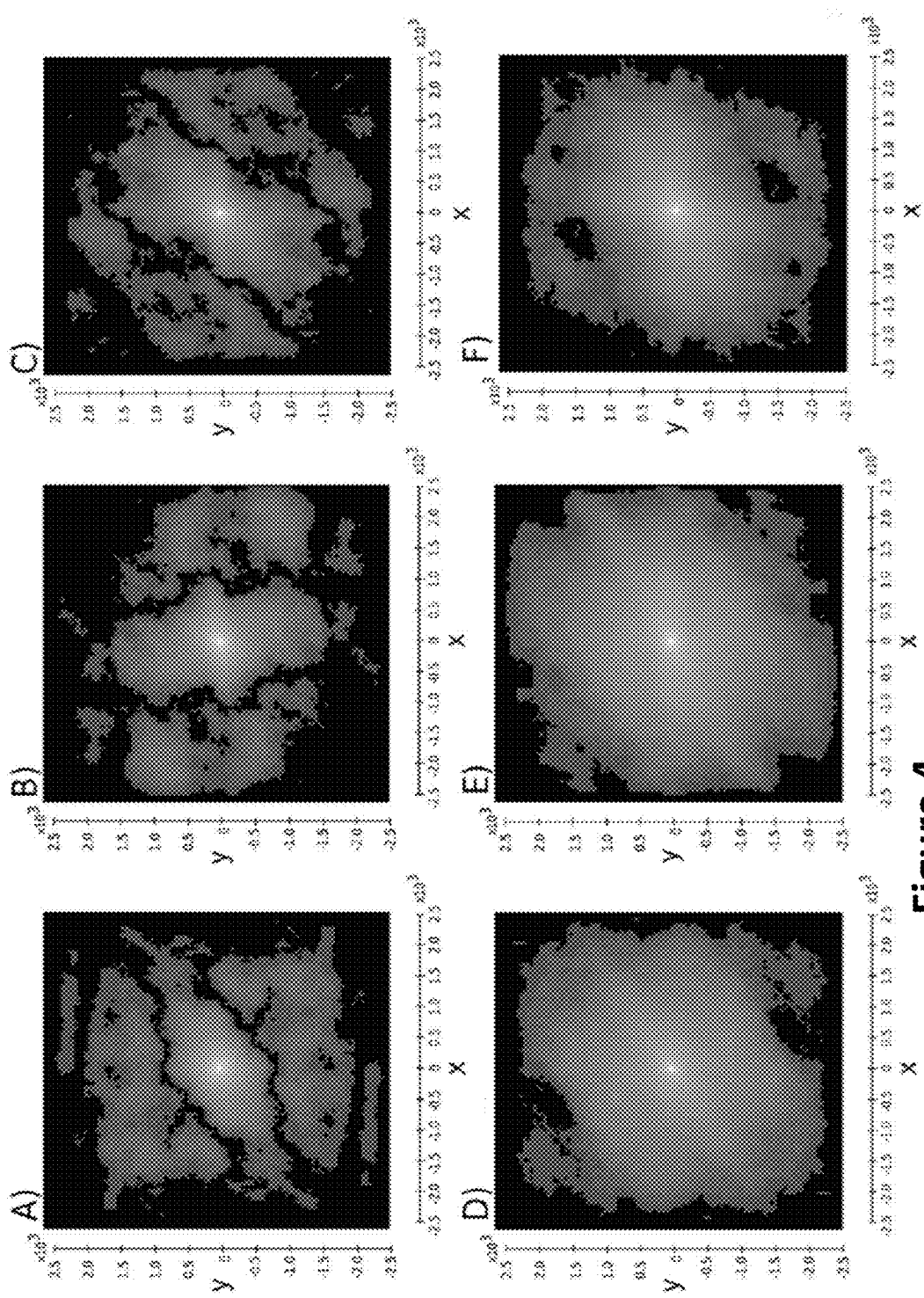
FIG. 4 illustrates 3-D autocorrelation functions of longitudinal relaxation time (T1) vasculature maps of amyloid positive mice (A-C) and amyloid negative mice (D-F).

A volume was selected that was representative of the cortex and hippocampus as shown in FIG. 2, and 3-D autocorrelation studies were conducted. The volume was C: 52"3 voxels. Volume C is a subset of Volume B. 3-D autocorrelation functions of the vascular maps within volume C are shown in FIG. 4 (FIG. 4 shows the 3-D autocorrelation functions of T1 vascular maps). The three images in the top row (A, B, C) correspond to amyloid positive transgenic mice, while the bottom row corresponds to the two age-matched amyloid negative mice (non-transgenic siblings, D and E) and a control C57BL/6 12 month old (F).

The characteristic structure of the amyloid positive mice is evident, with a marked fissure in the autocorrelation function, with $C_2$ rotational symmetry. In contrast, the normal and negative control mice exhibit a characteristic uniform structure, with also exhibiting $C_2$ symmetry. Thus, differentiating the two classes of structures is trivial; yet, the vascular structures themselves are visually unremarkable.

The correlation function is an indication of the extent of correlation between any two points in the domain, with a spacing equal to the argument of the correlation function. Thus, a perfect correlation (always obtained at zero displacement) is 1, while an uncorrelated event exhibits a correlation of zero. Therefore, the origin in each of the images in FIG. 4 is white, indicating that at zero displacement, the correlation is 1. Grayscale at other locations indicates a reduced correlation and black indicates no correlation. Thus, in the normal mice in the bottom row (D, E, F), there is a gentle drop off of correlation in all directions from the origin. The implication is that at any point in the vasculature (the domain sampled by the correlation function), there is a finite correlation with points surrounding it, as would be expected in a normal vascular map.

The characteristic fissure in the correlation function of the amyloid positive mice corresponds to a precipitous drop in the correlation function in that narrow region of the fissure. The fissures are rotationally symmetric ($C_2$), suggesting that there is anisotropic point symmetry ($D_{2n}$) in the vascular domain. Specific directions parallel to the fissures where there is no such drop off suggests that there are certain directions in the vascular domain where correlation is preserved.

F, also a normal mouse, shows somewhat different behavior, with small localized drops in correlation. The localized drops suggest very specific directional losses in correlation, but are clearly distinguishable from the drastic fissure structure of the amyloid positive cases.

Example 5—Simulation of Vascular Fissures

To determine the implications of the fissure structure on the correlation function in the vascular domain, fissures were simulated, starting with a normal vascular map (similar to the procedure described in Example 3). Anisotropic point symmetry ($D_{2n}$) would be consistent with blood vessels on which plaque-like dense objects were overlaid. Thus, in the axial direction of the vessels, there would be no drop in intensity, while at other angles there would be point symmetry about the reference center. On the other hand, if the plaques were not overlaid on the vessels, this symmetry would be destroyed.

Two cases were simulated. First, synthetic plaques were randomly distributed in the volume, interrupting blood vessels where overlap occurred. Second, synthetic plaques were distributed preferentially along the blood vessels. In both cases, plaques were assumed to exhibit a loss of intensity in the MR image, and appear similar to normal tissue.

Figure 5:
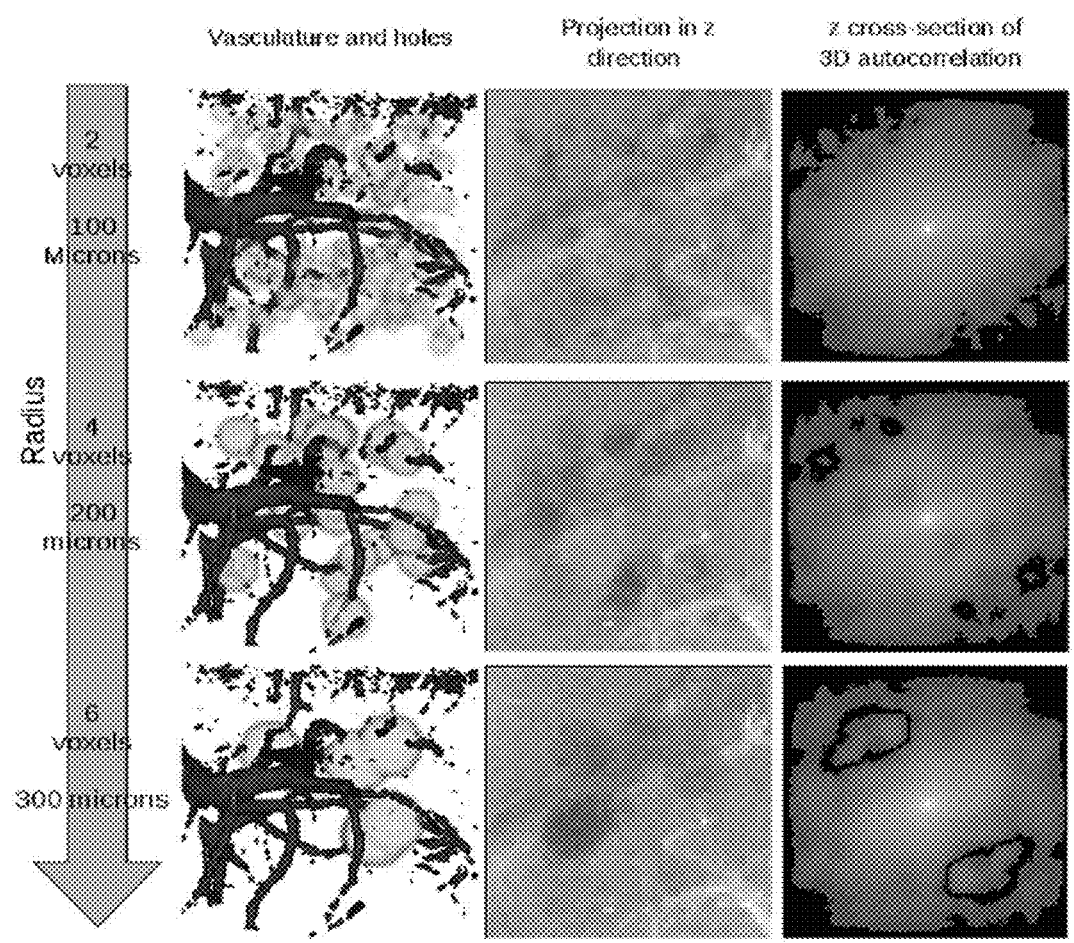
FIG. 5 illustrates 3-D autocorrelation analyses of cranial vasculature images, wherein the images have been randomly digitally manipulated to introduce synthetic "holes" that simulate amyloid plaques.

FIG. 5 shows an example of such "simulated" plaques overlaid on the otherwise normal vasculature of the selected tissue domain. Three cases are shown, with the average "plaque" size varying between 100μ and 300μ in radius, and occupying about 5% of the total volume of the tissue domain. The base case chosen is the vascular map for a normal 17 month old mouse (non-transgenic). The projections of the vascular images in the Z-direction (XY plane) and the Z-cross section (XY plane) of the autocorrelation function are shown. The autocorrelation function develops rotationally symmetric nodules of correlation loss, but does not share any traits with the correlation functions of amyloid positive mice.

Figure 6:
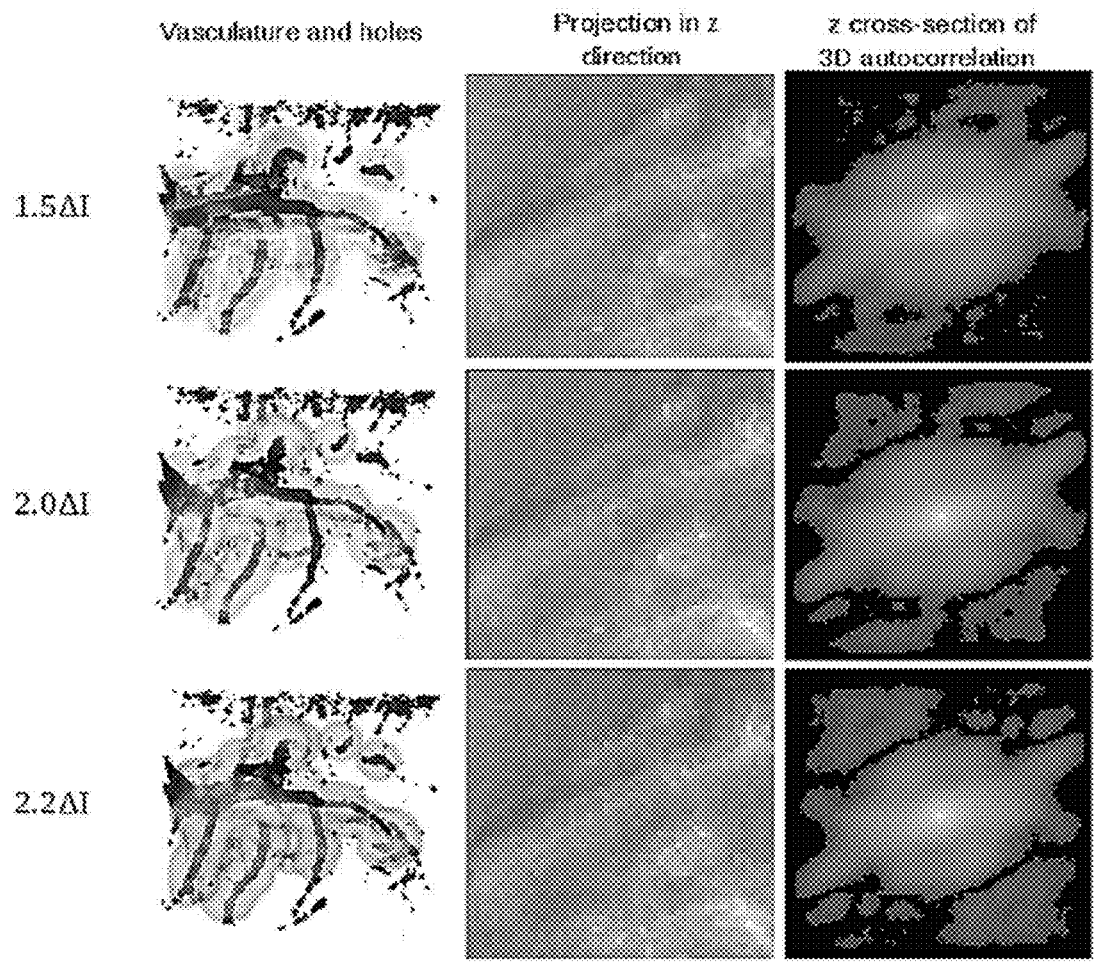
FIG. 6 illustrates 3-D autocorrelation analyses of cranial vasculature images, wherein the images have been digitally manipulated to introduce synthetic "holes" that simulate amyloid plaques along the vasculature structures in the tissues.

On the other hand, FIG. 6 shows the case of synthetic plaques distributed preferentially along the vasculature structures. The base case is the vascular map for a normal 17 month old mouse (non-transgenic). The plaques are shown with increasing image intensity (in multiples of ΔI, the 99% width of the unaltered image intensity distribution). Also shown in FIG. 6 are a 3-D rendering of the simulated plaques, a projection of the vascular map in the Z direction (XY plane), and the Z-cross section of the autocorrelation function for each case. The correlation maps clearly develop the rotationally symmetric fissure structure that is characteristic of the amyloid positive cases.

Thus, it may be concluded that: (1) normal mouse brain vasculature shows either a uniform autocorrelation function or, in some cases, due to noise in the vascular signal, an island structure in the correlation function, with local drops; and (2) amyloid mouse vasculature shows a characteristic fissure structure in the autocorrelation function, clearly distinguishable from all other forms.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When "only A or B but not both" is intended, then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." Finally, where the term "about" is used in conjunction with a number, it is intended to include ±10% of the number. For example, "about 10" may mean from 9 to 11.

As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art. Therefore, the application, in its broader aspects, is not limited to the specific details and illustrative examples shown. Departures may be made from such details and examples without departing from the spirit or scope of the general inventive concept.

What is claimed is:

1. A method for characterizing a pathological lesion in a patient, the method comprising:
   introducing into the patient a contrast enhancing agent;
   subjecting the patient to MRI to obtain a MRI image of a vasculature in the patient according to the contrast enhancing agent in the patient's blood;
   selecting a subdomain of interest of the MRI image;
   transforming the MRI image into at least one 3-D autocorrelation spectrum by applying a 3-D autocorrelation function to the subdomain of interest of the MRI image;
   analyzing the at least one 3-D autocorrelation spectrum and determining a characteristic fissure in the spectral domain that corresponds to the pathological lesion; and
   determining the subdomain of interest of the MRI image is normal or represents a pathological lesion according to the absence or presence of the characteristic fissure, thereby characterizing the MRI image for the pathological lesion.

2. The method of claim 1, further comprising comparing the at least one 3-D autocorrelation spectrum to a pre-existing 3-D autocorrelation spectrum that is characteristic for the pathological lesion.

3. The method of claim 1, wherein the contrast enhancing agent comprises:
   liposomes, the liposomes comprising:
      a phospholipid;
      a phospholipid that is derivatized with a polymer; and
      cholesterol,
   wherein at least one of:
      the liposomes encapsulate gadolinium compounds; and
      the liposomes chelate gadolinium compounds.

4. The method of claim 1, wherein the contrast enhancing agent comprises:
   liposomes, the liposomes comprising:
      DPPC;
      cholesterol; and
      mPEG2000-D SPE,
   wherein at least one of:
      the liposomes encapsulate gadolinium compounds; and
      the liposomes chelate gadolinium compounds.

5. The method of claim 1, wherein the contrast enhancing agent comprises a gadolinium chelate.

6. The method of claim 1, the characteristic fissure corresponding to $D_{2n}$ anisotropic point symmetry in the vascular domain.

7. The method of claim 1, the characteristic fissure in the at least one 3-D autocorrelation spectrum comprising a $C_2$ symmetric fissure.

8. A method for detecting amyloid plaque deposition on a patient's brain, the method comprising:
   introducing into the patient a nanoparticle contrast enhancing agent;
   selecting a subdomain of interest of the MRI image;
   subjecting the patient to MRI to obtain a MRI image of a vasculature in the patient's brain according to the nanoparticle contrast enhancing agent in the patient's blood;
   transforming the MRI image into at least one 3-D autocorrelation spectrum by applying a 3-D autocorrelation function to the subdomain of interest of the MRI image;
   analyzing the at least one 3-D autocorrelation spectrum and determining a characteristic fissure in the spectral domain that corresponds amyloid plaque deposition; and
   determining the subdomain of interest of the MRI image is normal or represents amyloid plaque deposition according to the absence or presence of the characteristic fissure,
   thereby detecting amyloid plaque deposition in the patient's brain.

9. The method of claim 8, further comprising comparing the at least one 3-D autocorrelation spectrum to a pre-existing 3-D autocorrelation spectrum that is characteristic for amyloid plaque deposition on a brain.

10. The method of claim 8, wherein the nanoparticle contrast enhancing agent comprises:
    liposomes, the liposomes comprising:
    a phospholipid;
    a phospholipid that is derivatized with a polymer; and
    cholesterol, wherein at least one of:
the liposomes encapsulate gadolinium compounds; and
the liposomes chelate gadolinium compounds.

11. The method of claim 8, wherein the nanoparticle contrast enhancing agent comprises:
liposomes, the liposomes comprising:
DPPC;
cholesterol; and
mPEG2000-D SPE,
wherein at least one of:
the liposomes encapsulate gadolinium compounds; and
the liposomes chelate gadolinium compounds.

12. The method of claim 8, wherein the nanoparticle contrast enhancing agent comprises a gadolinium chelate.

13. The method of claim 8, the characteristic fissure corresponding to $D_{2n}$ anisotropic point symmetry in the vascular domain.

14. The method of claim 8, the characteristic fissure in the at least one 3-D autocorrelation spectrum comprising a $C_2$ symmetric fissure.

15. A method for diagnosing determining the presence of amyloid plaque deposition which has been linked to Alzheimer's Disease in a patient, the method comprising:
introducing into the patient a nanoparticle contrast enhancing agent, the nanoparticle contrast enhancing agent comprising:
liposomes, the liposomes comprising:
DPPC;
cholesterol; and
mPEG2000-DSPE,
wherein at least one of:
the liposomes encapsulate gadolinium compounds; and
the liposomes chelate gadolinium compounds;
subjecting the patient to MRI to obtain a MRI image of a vasculature in the patient's brain according to the nanoparticle contrast enhancing agent in the patient's blood;
selecting a subdomain of interest of the MRI image;
transforming the MRI image into at least one 3-D autocorrelation spectrum by applying a 3-D autocorrelation function to the subdomain of interest of the MRI image;
analyzing the at least one 3-D autocorrelation spectrum for a characteristic fissure in the spectral domain that corresponds to amyloid plaque deposition which has been linked to Alzheimer's Disease; and
determining the subdomain of interest of the MRI image is normal or represents the presence of amyloid plaque deposition which has been linked to Alzheimer's Disease according to an absence or presence, respectively, of the characteristic fissure.

16. The method of claim 15, further comprising comparing the at least one 3-D autocorrelation spectrum to a pre-existing 3-D autocorrelation spectrum that is characteristic for Alzheimer's Disease.

17. The method of claim 15, wherein the molar ratio of the DPPC, the gadolinium compounds, the cholesterol, and the mPEG2000-DSPE is about 30:25:40:5.

18. The method of claim 15, wherein the liposomes have an average diameter of less than about 150 nm.

19. The method of claim 15, one or more of:
the characteristic fissure corresponding to $D_{2n}$ anisotropic point symmetry in the vascular domain; and
the characteristic fissure in the at least one 3-D autocorrelation spectrum comprising a $C_2$ symmetric fissure.

20. The method of claim 15, the patient being a living patient.

* * * * *